US006423301B1

(12) United States Patent
Cox

(10) Patent No.: US 6,423,301 B1
(45) Date of Patent: Jul. 23, 2002

(54) ACID RESISTANT FILM FORMING DENTAL COMPOSITION AND METHOD OF USE

(75) Inventor: Charles F. Cox, Fenton, MI (US)

(73) Assignee: Jeffrey S. Cox, Fenton, MI (US)

( * ) Notice: Subject to any disclaimer, the term of this patent is extended or adjusted under 35 U.S.C. 154(b) by 0 days.

(21) Appl. No.: 09/929,177

(22) Filed: Aug. 14, 2001

Related U.S. Application Data

(63) Continuation-in-part of application No. 09/250,443, filed on Feb. 16, 1999, now abandoned.

(51) Int. Cl.[7] ................................................. A61K 7/16
(52) U.S. Cl. ...................................... 424/49; 433/217.1
(58) Field of Search ..................... 424/49–58

(56) References Cited

U.S. PATENT DOCUMENTS

| | | | | |
|---|---|---|---|---|
| 2,876,083 A | * | 3/1959 | Prietl | 23/295 |
| 3,510,266 A | * | 5/1970 | Midler (I) | 23/273 |
| 3,892,539 A | * | 7/1975 | Midler (II) | 23/301 R |
| 4,057,621 A | * | 11/1977 | Pashley et al. | 424/49 |
| 4,378,228 A | * | 3/1983 | Beatty et al. | 23/300 |
| 4,538,990 A | * | 9/1985 | Pashley | 433/217 |
| 5,020,731 A | * | 6/1991 | Somoza et al. | 241/1 |
| 5,471,001 A | * | 11/1995 | Anderson et al. | 562/593 |
| 5,609,998 A | * | 3/1997 | Texter et al. (I) | 430/449 |
| 5,750,321 A | * | 5/1998 | Texter et al. (II) | 430/449 |
| 5,874,066 A | * | 2/1999 | Hack et al. | 424/49 |
| 5,906,809 A | * | 5/1999 | Hack et al. | 424/49 |
| 5,994,041 A | * | 11/1999 | Texter et al. (III) | 430/466 |

FOREIGN PATENT DOCUMENTS

| | | | |
|---|---|---|---|
| WO | 2000048562 A1 | * | 8/2000 |

OTHER PUBLICATIONS

Kueppers J. Cryst. Growth 15(2): 89–92, 1972.*
Kueppers et al. AETA Crystallogr. 26(pt. 4) 401–405 Sect. A Williams, 1970.*
Follner Z. Anorg. Allg. Chom. 370(5–6) 235–237, 1969.*
Kueppers Z. Kristallogr. Kristallcerom. Kristauphy Kristawhom Mo(5–6) 393–398, 1974.*
Verdonk Therm. Anal. Proc. Int. Conf. 3rd 1971(19721 vol. 2: 651–666, 1971.*
Higashiyama et al. Rop. Res. Lab. Surf. Sci. Okayama Univ. 2(6): 301–317, 1966.*
Chandra Phys. Status Solid A 64(1): 395–405, 1981.*

* cited by examiner

*Primary Examiner*—Shep K. Rose
(74) *Attorney, Agent, or Firm*—W. Dennis Drehkoff; Ladas & Parry

(57) ABSTRACT

A method of decreasing the permeability of dentin by the application of an effective amount of oxalic acid potassium salt, dihydrate is an aqueous solution at a pH of about 2.0 to 4.0 to the dentin.

6 Claims, No Drawings

ACID RESISTANT FILM FORMING DENTAL COMPOSITION AND METHOD OF USE

This application is a continuation-in-part of Ser. No. 09/250,443 filed Feb. 16,1999, now abandoned.

BACKGROUND OF THE INVENTION

1. Field of the Invention

Individuals often report an immediate increase in dentin postoperative hypersensitivity or pain to sudden extremes of thermal stimuli to either a particular tooth or a group of teeth. This may occur following either the replacement of a restoration due to a recurrent carious lesion subjacent to a previously placed restoration, the initial placement of an existing amalgam alloy or a tooth colored resin composite restorations or following the bleaching of teeth with power (light, heat or other) assisted forms of tooth whitening systems. Patients may simply be cautioned by the dentist to be aware of an immediate increased feeling of pain to a rapid jet of air, cold drinks, to chewing forces of occlusion or to other factors such as acidic foods. Stimuli, such as cold water, cool air, osmotic gradient shifts, or sweet or acidic solutions at the cavosurface margin of a restoration have all been shown to cause an immediate increase in the dentin pain response. Dentists may simply call this phenomenon as patient dentin pain (postoperative hypersensitivity/DPH) or simply dental discomfort. Often patients are told by the dentist to simply wait a few days or weeks and that the pain of discomfort will become less and less, and eventually that it should go away.

The acute, sharp, piercing pain of dentin pain is often a fairly common complaint among many patients who have recently received a amalgam alloy or resin composite restoration in vital dentin that has been treated with a conventional dentin liner such as a calcium hydroxide $Ca(OH)_2$ material such as Dycal® or Life®. Dentin postoperative hypersensitivity generally occurs with the normal physiological breakdown of the smear layer or its removal at the cavosurface margin due to oral fluids which reach an acidic pH of 2.7 to more neutral at pH 6.0.

If the dentist uses any type of instrumentation, for example, rotary instrumentation with a drill or bur, scraping or polishing with any sort of hand instrument, will leave a layer of debris on the tooth surface called a smear layer. The breakdown of the smear layer by physiological action or by the dentist, opens and exposes the dentinal tubule complex to a bi-directional flow of fluids from the dental pulp (Pashley, 1981 Arch. Oral. Biol. 26: 703–706). It is this increased bi-directional fluid flow which is responsible for the patients' dentin postoperative hypersensitivity to cold or rapid air flow.

Many patients experience dentin postoperative hypersensitivity when an existing amalgam alloy or a resin composite restoration and its underlying $CA(OH)_2$ base of Dycal® or Life® washes out or is removed and the dentin looses its biological seal or simply feel the pain from discomfort due to premature occlusal contact or thermal or cold extremes.

The physiological mechanism for dentin pain following placement of either an amalgam alloy or a resin composite restoration has been explained as being due to the breakdown or loss of the smear layer which then results in an immediate increased flow of pulpal fluids though its micro channel complex (Pashley, et al. 1984 Arch. Oral. Biol. 29:65–68). This increase in flow may be 94% greater than the normal physiological flow of fluids through the normal dentin substrate.

The present invention relates to the use of an acid resistant film forming liner material that occludes the dentinal tubules to decrease dentinal sensitivity, acid penetration and discomfort.

2. Summary of the Related Art

The afore mentioned Pashley et al., articles disclose the hydrodynamic theory of flow and displacement of the contents of dental tubules under various conditions. Pain stimuli is transmitted to nerve structure by hydrodynamic movement of force in the tubules within the dentin. Prior art methods of alleviating pain during dental restoration procedures includes preparing a cavity in a tooth to receive restorative material with a cavity liner or cavity varnishes. The material allegedly decreases the permeability of the dentin to any other materials placed in the cavity during this restoration in addition to blocking the attack of any microleakage, that is, contaminants tom the oral fluids that may attempt to penetrate the cavity In the event that the restorative material permits microleakage around its margins with the tooth. Prior art cavity varnishes frequently contain organic gums dissolved in organic solvents. The organic solvent evaporates leaving a film of the organic gum on the dentin.

These cavity lining agents are composed primarily of water and soluble organic materials which is often placed on a liquid layer that covers the surface of the dentin without any bonding. This may weaken any adherence of the cavity varnish to the tooth surface and may cause leaking.

A natural cavity liner is microcrystalline debris which is found in the surface of dentin which is cut and is referred to as a smear layer. The smear layer occludes the orifices of the dentinal tubules to the point where bacteria cannot access the tubules. However, the smear layer is often destroyed due to the acidity in the oral cavity and the presence of microleakage around the filling material which is in contact with a cavity varnish.

The prior art also includes the use of oxalate salts to desensitize hypersensitive dentin or cementum surfaces on teeth, for example, as disclosed in U.S. Pat. No. 4,057,621. 4,538,990 discloses a two-step method using different oxalate acids salts to decrease the permeability of a dental cavity prepared for receiving a restorative material. The method involves sequential application of the oxalate salts to the smear layer. First, a 1 to 30% weight to volume neutral oxalate salt solution, for example, dipotassium oxide is applied and then followed within one or two minutes by an application of 0.5 to 3% weight to volume percent of an acidic oxalate solution, such as monopotassium mono hydrogen oxalate. The neutral oxalate forms large calcium oxalate crystals over the dentin surface and the acid oxalate forms smaller crystals around the previously precipitated larger crystals to form a uniform layer of crystals.

U.S. Pat. No. 2,746,905 discloses the use of dehydroacetic acid and the soluble salts to maintain the pH of the mouth to about 5.2 to prevent the dissolution of inorganic tooth enamel material which includes the use of oxalate in the composition as an enamel protective agent to increase the resistance of the tooth to acid attack.

In contrast to the above literature and patents, the present invention utilizes a specific oxalic acid salt, oxalate acid potassium salt, dihydrate, 99% which when applied to the surface of the tooth penetrates into the tubules and fibriles of the dentin layer. The oxalic acid potassium salt dihydrate, or it may be simply referred to as potassium oxalate dihydrate, eliminates fluid movement within the tubules and therefore limits the dentin to be incapable of transmitting painful stimuli to the pulp in the form of fluid movement Therefore, no pain or discomfort is felt by the patient for long periods of time.

SUMMARY OF THE INVENTION

The present invention relates to a method of utilizing a solution of oxalic acid potassium salt, dihydrate, 99% as referred to hereinafter as potassium oxalate dihydrate to react with ionized calcium in the dentinal fluid forming an insoluble white precipitate of calcium oxalate that includes the dentinal tubules. This action leads to decreased permeability of dentin, decreased acid penetration of dentin and decreased dentinal sensitivity. The solution of potassium oxalate dihydrate contains about 1.5 to about 10% by weight oxalic acid potassium salt dihydrate and has a pH ranging from about 2.0 to about 4.0.

It is an object of the present invention to provide a method of using a solution of oxalic acid potassium salt dihydrate to decrease permeability of dentin.

Another object of the present invention is to provide a method of using a solution of oxalic acid potassium salt dihydrate to decrease dentin sensitivity.

Another object of the present invention is to provide a method of using a solution of oxalic acid potassium salt dihydrate to decrease acid penetration of dentin.

And, yet another object of the present invention is to provide a simple diagnostic test to determine if dental pain or discomfort is reversible or irreversible.

Another object of the present invention is to provide a method to solubilize oxalic acid potassium salt dihydrate in water so that it is available in a dosage form to serve as a densensitizing agent

DETAILED DESCRIPTION OF THE INVENTION

The mechanism action of the potassium oxalate as well as its effectiveness in reducing dental sensitivity had been reported by Pashley, et al. in the literature, see Pashley, D. H. et. al. (1983): Dentin Permeability—Effects of Desensitizing Dentrifices In Vitro, *J. Periodontol.* 55: 522–525; Pashley, D. H. and Gallloway (1985): The Effects of Oxalate Treatment on the Smear Layer of Ground Surfaces of Human Dentine. *Arch Oral. Biol.* 30: 731–737; Pashley, D. H. (1989): Dentin: A Dynamic Substrate—A Review. *Scanning Micros* 3: 161–176; Pashley, E. L. et al. (1989) Dentin Permeability and Bond Strengths after Various Surface Treatments. *Dent. Mater* 5: 375–378.

Pashley, et. al. discloses a potassium oxalate form of protective layer of insoluble calcium oxalate on the surface of the exposed dentin that occludes open tubules. The occlusion causes a decrease in hydroconductance and tubule permeability as well as a decrease in acid penetration and, ultimately a reduction in dentinal sensitivity. U.S. Pat. No. 4,057,621 discloses potassium oxalate compounds useful in the invention comprising a method of desensitizing hypersensitive dentin and cementum. In the method, a member selected from the group consisting of a mono and di-substituted alkali mental and ammonium oxalate in an aqueous solution is applied in an effective amount to the dentin and cementum to desensitize the area. Compounds disclosed in the patent include the following, which are shown with their water solubility. They are described in the 54th and 76th Editions, *Handbook of Chemistry and Physics* (1973–74 and 1995–96).

| | |
|---|---|
| Dipotassium oxalate ($K_2C_2O_4 \cdot H_2O$) | 33.0 Hot Water Solubility |
| Potassium hydrogen oxalate ($KHC_2O_4$) | 16.7 Hot Water Solubility |
| Sodium oxalate ($Na_2C_2O_4$) | 6.33 Hot Water Solubility |
| Sodium hydrogen oxatate ($NaHC_2O_4 \cdot H_2O$) | 21.0 Hot Water Solubility |
| Lithium oxatate ($Li_2C_2O_4$) | 8.0 Cold Water Solubility |
| Lithium hydrogen oxalate ($LiHC_2O_4 \cdot H_2O$) | No reading |
| Ammonium oxalate [$(NH_4)_2C_2O_4 \cdot H_2O$] | 11.8 Hot Water Solubility |
| Hydrogen oxalate ($NH_4HC_2O_4 \cdot H_2O$) | No reading |

The active ingredient in the present invention is oxalate acid potassium salt, dihydrate 99% with a molecular weight of 254.19 and a formula of $C_4 H_3 KO_8 \cdot 2H_2O$ The oxalate potassium salt, dihydrate 99% or referred to herein as potassium oxalate dihydrate is a white crystaline powder that is slightly soluble in water, having a solubility of 29 Gm/liter. The potassium oxalate dihydrate is utilized preferably in an aqueous solution. Dissolving the potassium oxalate dihydrate in water may be difficult under conventional practices, however, the product of the present invention is subjected to ultrasonic frequencies to disperse the large crystals of the potasium oxalate in water and and therefore solubilize in water. This treatment renders the potassium dihydrate into a particle size which is adequate and sufficient for the purposes of this invention. Any treatment to solubilize the potassium oxalate dihydrate in water will be satisfactory, however, the use of variable high frequency sound waves is preferred.

In order to prepare the product of the present invention, double distilled deionized water, with a water purity of 1,000,000 to 5,000,000 resistance in ohms, according to standardized testing of the American National Standards Institute. The high resistance equates to high purity. Other forms of purified water may be utilized, however, the double distilled deionized wazter is preferred. Sufficient oxalic acid potassium salt, dihydrate 99% crystals are added to the water so that the amount in the final solution ranges from 1.5% to 4.0% weight to volume. Preferably, the amount is about 2.9% by weight in the final product. The water and crystals are then subjected to variable ultra high frequency wave action to disintegrate the crystals into very small particles to form a solution. This is typically accomplished by using an ultrasonic cell disrupter, however, any means can be used to solubilize the oxalic acid potassium salt, dihydrate. Preferably, an ultrasonic cell disruptor such as identified as the Branson Sonifier or equivalent can be utilized. The sonifier converts electrical energy from a power supply to mechanical vibration. In this apparatus, the water and potassium oxalate dihydrate crystals are placed in a mixing container and attached to a pumping system. The pump is started to circulate the water in a continuous flow at about ½ liter per minute. The water and crystals are circulated in the chamber for about 30 minutes. This process uses a variable ultra high frequency wave focused in a small chamber directly on the crystals in the water. The mechanical vibration may range to 20,000 Hz. In use, the preferred vibrations are at a frequency of about 16,000 Hz to about 20,000 Hz at the tip of the ultrasonic horn as it disrupts and disintegrates the crystals into very small particles to so that they go into solution. The water and crystal mixture passes the ultrasonic horn multiple times which: continues to disintegrate the crystals into smaller particles each time it passes. Preferably, the particle size in the final product approximates about 5 microns to about 15 microns when viewed under an 100 power microscope. After solublization, no precipate is visible after 24 hours with the unaided human eye. Larger particles sizes are acceptable, however, particle sizes in the range of about 5 microns to 15 microns are preferered, and most preferably the particle size is about 10 microns.

The acidic solution has a pH ranging from about 2.0 to 4.0 with the preferred range being about 2.7 to about 3.0. Most preferably, the pH is 3.0. The pH of the acidic solution is controlled by the amount of potassium oxalate dihydrate that is used in the formulation. The larger the amount of the potassium oxalate dihydrate the lower the pH.

In operation, the use of potassium oxalate dihydrate is a one step process to stop sensitivity to cold and air immediately. It is also helpful as a diagnostic aid to assist the dentist in differentiating between reversible fluid flow in dentin and nonpulp inflammation and irreversible fluid flow which is results in pulp inflammation. About 3–6 drops of potassium oxalate dihydrate can be placed in a clean Dappen dish using forceps so that a small, sterile cotton pallet can be saturated with the potassium oxalate dihydrate which is then gently rubbed or dabbed onto the affected tooth area for at least thirty seconds. The solution may be gently rubbed around the margin or over the crown cementum or exposed root surfaces as well as onto the exposed root of teeth which are sensitive to cold or air stimuli. Brushing the product on the tooth surface is not necessary and should not be accomplished. No rinsing is needed. After application, a gentle air dispersion may be applied to the surface to evaporate the solution from the area leaving a frosty white surface which is an acid resistant mineral layer that stops fluid movement or dentin hypersensitivity to cold and air stimuli. It is not necessary to blast air on the tooth surface because it could remove the solution.

The product of the present invention can be applied on prepared tooth structure such vital dentin both before and after oral hygiene treatment for prophylaxis for cleaning and scaling. The product may be used as a one-step replacement under all crowns and inlays with veneer preparation. It can be used on dentin of all cavity preparation for amalgam alloys, and resin composite restoration. The acid resistant film forming liner material can have bonding materials applied directly on its surface for binding restorative materials. It may also be applied on the tooth surface following a bleaching procedure whether the procedure is done in a dentist's office or if the patient uses a home bleaching kit. In addition, the potassium oxalate dihydrate solution can be used as a diagnostic tool to differentiate between acute dentinal pain and chronic pulpual pain. Acute dentin pain is generally called a reversible tooth pain. To the dentist and patient, this means that there is a defect located within the substance of the dentin and not within the nerves within the dental pulp. The problem is reversible without any invasive endodontic treatment. Alternatively, chronic dental pain is an irreversible stiumulus which indicates that the nerves of the dental pulpual are inflammed and must be removed by some sort of biomechanical endodontic instrumentation. The potassium oxalate dihydrate of the present invention provides a simple one-step diagnostic treatment that allows the dentist to discriminate reversible and irreversible dental pain. When a patient complains of pain to cold and air and there are no diagnostic features of radiographic presence of a periapical radiolucency, fractured tooth root or other obvious clinical problems then the dentist may simply rub the potassium oxalate dihydrate of the present invention onto and around edges or cavosurface margins of the tooth restoration interface. If the patient reports an immediate cessation to dential pain then the dentist may complete the diagnosis that the problem is fluid flow in the dentin or microleakage. This is comfirmation of reversible pulp inflammation and may be treated by the repair of the restoration and not the removal of the pulp.

In order to explain the mechanism of action of the present invention, the following is a description of the mode of action of the present invention used in, for example, a restorative procedure. However, the mode of action is similar for all applications. Acidic solution of potassium oxalate dihyrate of the, present invention initially serves to break down the smear layer and opens the substrate of dentin, as well as enamel and cementum. Buffering occurs to the pH of the potassium oxalate dihydrate and as the reaction progresses, the pH of the solution the moves toward neutrality. Simultaneously, the calcium granular particles precipitate on the entire cavity surface in addition to any small physiological cracks which are normally present in adult enamel and or cementum of the root surface. This granular precipitate, when dried, is an acid resistant lining layer that is chemically bound to the surface as well as into the dentinal tubules of the cavity. Once the granular crystals are formed, the barrier effect is immediately felt by the patient. To the unaided eye, there is a slightly whitish film that may be seen on the surface of the cavity and tooth.

EXAMPLE I

Preparation Of Solution

Twenty-nine (29) grams of oxalate potassium salt, dihydrate 99%, a white crystalline substance, were added to one liter of double distilled deionized water in a mixing container. The container is capped and affixed to a Branson Sonifer manufactured by Branson Ultrasonic Corporation of Danbury, Conn. The feed and return hoses were connected between the container and sonifer. The pump on the sonifer was started to recirculate the water at a setting of ½ liter per minute. The sonifer was started at a setting of constant duty cycle, time on hold, output control at 0.9 or 18,000 Hz.

The water was subjected to ultrasonic vibrations for 30 minutes. The water was allowed to set for 30 minutes and samples were taken for viewing under a 100×power microscope. The size of the cystals was about 10 microns.

EXAMPLE 2

Clinical Evaluation

To show the desensitization properties of the potassium oxalate dihydrate of the present invention, amalgam restoration patients were treated with a commonly used, commercially available cavity varnish or the product of the present invention prior to placement of an amalgam. Prior to anesthesia for pre-treatment evaluation and during the first week of treatment, the patients completed a questionnaire on pain. The patients were also evaluated post-operatively at one, three and six weeks. The results of the study demonstrate a reduction in post-operative hypersensitivity, especially cold, in patients treated with the potassium oxalate dihyrate of the present invention.

Materials and Methods

A total of 65 human teeth with active carious lesions precluding either acute or chronic dentin postoperative hypersensitivity symptomatology were selected to be restored with the commercially available amalgam alloy Tytin®. Only patients who had elected amalgam restoration procedures at UAB were employed for this study. Each tooth received a pre anesthesia evaluation for dentin postoperative hypersensitive with a cold stimulus and air jet for thermal testing. For cold-ice testing, plastic needle covers were filled with water and frozen in a refrigerator freezer for uses as the standardized cold stimulus.

For air stimulation, the standardized baseline air jet from a syringe was used to direct a blast of air at the offending tooth and defective restoration. A randomized number chart was employed to select teeth for either the Copalite® varnish controls orteeth to be treated with the product of the present invention, potassium oxalate dihydrate.

Amalgam Preparations

Following pre operative data collection and anesthesia, each tooth then received a routine intracoronal Class-I or Class-II cavity preparations.

All 65 teeth (35 intracoronal Copalite® controls and 30 teeth to be treaed with the product of the present invention, potassium oxalate dihydrate, received Class-I or Class-II cavity preparations—prepared with either a new #245 or #330 carbide bur at ultra high speed, under water spray and high speed evacuation. Following cavity preparation, rinsing and gentle air drying, the entire preparation surface was treated with the Copalite® varnish without modification or removal of the smear layer. Each control cavity was treated with three layers of copal varnish and each layer gently air dispersed with a chip syringe before the following Copalite® coat was applied. A metal matrix was placed on all Class II cavity preparations and the tooth was restored to anatomical contour with the dispersed phase spherical amalgam alloy Tytin.

All other clinical preparation procedures, testing criteria and recalls were identical to those employed with the 39 teeth treated with the product of the present invention. An additional 30 teeth were treated with the product of the invention, potassium oxalate dehydrate. Following intracoronal Class-I or Class-II cavity preparations for caries removal, the cavity was cleaned with sterile water, gently air dispersed and the prepared cavity surface treated twice with potassium oxalate dihyrate. The potassium oxalate dihydrate solution was dispensed into a clean Dappen dish and then absorbed into a sterile cotton pellet. The entire surface area of the cavity of prepared enamel and dentin surface was mechanically swabbed for approximately 2 minutes, air dispersed and again treated as before. The surface was gently air dried, the matrix placed and the cavity restored with Tytin®.

Prior to anesthesia for pretreatment evaluation and during the 1st week of treatment, the patient was recalled to the clinic to fill out a form as to their own perception of "feeling" or response to various stimuli, including cold, hot, sweets, biting, and brushing. The patient was also evaluated for postoperative hypersensitivity at one, three and six weeks post-operatively. The subjective consideration of patients' data were collected by having the patient cross the 10 cm line at a point where they felt their range of pain was indicated. The McGill Visual analog scale was noted at each time interval. Thermal tests for ice and an air jet were administered and data recorded as for all of the previous tests.

For base line data, each patient was evaluated for pain or sensitivity to cold and air prior to their treatment in this study. A total of 35 patients were treated in the control in the Copalite® group and 30 patients were treated in the potassium oxalate dihydrate group—for a total study group of N=65.

All data was analyzed by one-way Analysis of Variance (ANOVA) at the 0.05 level depending on the cell sizes in our contingency table of treatments versus responses. Differences between the various groups within the ANOVA was compared using the Student T test ($p<0.050$).

Results

Questionnaire Responses

Responses from each of the patients were recorded on separate sheets and then tabulated onto the master sheet according to the identified criteria. The raw data were recorded from the McGill Visual Analog Scale (MVAS) evaluation sheets. Data were recorded from all patients experiencing none, some or severe post-operative hypersensitivity based on the patient responses at the various intervals, preoperative at 0 days, and post treatment 5, 7, 21 and 42 days. In each case responses were reported to the various test stimuli; cold, hot, sweet, biting of percussion, and brushing and flossing. Evaluation forms were completed.

The date for each of the McGill VA scales were tabulated and recorded on a separate sheet with the patient's name and clinical record number—as a 10 centimeter straight line with no identifying marks along its axis.

Approximately 12% of the patients experienced some sort of preoperative hypersensitivity, in response to questions concerning pain—mostly to the cold stimulus. However, 65% of the patients claimed some sort of pre-operative response on the MVA scale—of which over ½ of these patients (52%) marked values of 0–1 mm on a scale on the 10 centimeter pre-operative scale. Only 2% of the total population experienced any pre-operative pain greater than 5 mm on the 10 centimeter MVA scale.

Following routine caries excavation, application of potassium oxalate dihydrate or Copalite control solutions, and placement of the amalgam restoration, patients showed a reduction in sensitivity postoperatively. In those individuals who had received the control Copalite® treatment, there was a 2.3% reduction in sensitivity to the various stimuli (especially cold), in response to direct questioning. However, among the patients treated with the potassium oxalate dihydrate of the present invention, there was an overall reduction in their reported pain by a level of 80.3%.

The collective data from the MVA scale show a dramatic reduction in post-operative pain in those teeth which were treated with potassiumoxalate dihydrate while only 68.7% of the Copalite® patients exhibited temporary pain reduction post-operatively.

The data show that for the cold discriminator measurement there was a greater reduction in overall pain reduction with Super Seal than the commercially available Copalite®. Furthermore, patient responses to the MVA survey document showed the majority of individuals experience no post operative pain with the product of the present invention, potassium oxalate dihydrate. Overall, 25.7% of the patients treated with Copalite® and 88.5% of those patients' teeth treated with potassium oxalate dehydrate were pain free following the first procedure

TABLE 1

PATIENT RESPONSE DATA - Amalgam Alloy Study
35 Copalite ®    30 Super Seal    Total Restorations = 65

| STIM-ULUS | PAIN | MATERIAL MATERIAL | Pre Treatment | 5 Days | 7 Days | 21 Days | 42 Days |
|---|---|---|---|---|---|---|---|
| Cold | Severe | Copalite ® | 0 | 0 | 0 | 0 | 0 |
|  |  | Super Seal | 0 | 0 | 0 | 0 | 0 |
|  | Some | Copalite ® | 8 | 7 | 7 | 4 | 3 |
|  |  | Super Seal | 8 | 1 | 0 | 0 | 0 |
|  | None | Copalite ® | 27 | 28 | 28 | 31 | 32 |
|  |  | Super Seal | 22 | 29 | 30 | 30 | 30 |

TABLE 1-continued

PATIENT RESPONSE DATA - Amalgam Alloy Study
35 Copalite ®     30 Super Seal     Total Restorations = 65

| STIMULUS | PAIN | MATERIAL | Pre Treatment | 5 Days | 7 Days | 21 Days | 42 Days |
|---|---|---|---|---|---|---|---|
| Hot | Severe | Copalite ® | 0 | 0 | 0 | 0 | 0 |
|  |  | Super Seal | 0 | 0 | 0 | 0 | 0 |
|  | Some | Copalite ® | 0 | 1 | 1 | 2 | 2 |
|  |  | Super Seal | 0 | 0 | 0 | 0 | 0 |
|  | None | Copalite ® | 35 | 34 | 34 | 33 | 33 |
|  |  | Super Seal | 30 | 30 | 30 | 30 | 30 |
| Sweets | Severe | Copalite ® | 1 | 1 | 1 | 1 | 1 |
|  |  | Super Seal | 0 | 0 | 0 | 0 | 0 |
|  | Some | Copalite ® | 0 | 1 | 1 | 2 | 2 |
|  |  | Super Seal | 2 | 1 | 0 | 0 | 0 |
|  | None | Copalite ® | 34 | 33 | 33 | 32 | 32 |
|  |  | Super Seal | 28 | 29 | 30 | 30 | 30 |
| Biting Sensitivity | Severe | Copalite ® | 0 | 0 | 0 | 0 | 0 |
|  |  | Super Seal | 0 | 0 | 0 | 0 | 0 |
|  | Some | Copalite ® | 1 | 1 | 1 | 1 | 1 |
|  |  | Super Seal | 4 | 5 | 1 | 2 | 2 |
|  | None | Copalite ® | 34 | 34 | 34 | 34 | 34 |
|  |  | Super Seal | 26 | 25 | 29 | 28 | 28 |
| Brushing Flossing | Severe | Copalite ® | 0 | 0 | 0 | 0 | 0 |
|  |  | Super Seal | 0 | 0 | 0 | 0 | 0 |
|  | Some | Copalite ® | 2 | 2 | 3 | 3 | 3 |
|  |  | Super Seal | 4 | 1 | 0 | 0 | 0 |
|  | None | Copalite ® | 33 | 33 | 32 | 32 | 32 |
|  |  | Super Seal | 26 | 29 | 30 | 30 | 30 |

Complete test results are shown in Table 1. The product of the invention is defined as Super Seal in the table.

It should be understood that the foregoing disclosure emphasizes certain specific embodiments of the invention and that all modifications or alternatives equivalent thereto are within the spirit and scope of the invention set forth herein.

What is claimed is:

1. A method of decreasing the permeability of dentin comprising applying to the dentin an effective amount of oxalic acid potassium salt, dihydrate in a aqueous solution, the concentration of the oxalic acid potassium salt dihydrate ranging from about 1.5% about 10.0% by weight and the solution having a pH in the range of about 2.0 to about 4.0.

2. The method of claim 1 wherein the effective amount of oxalic acid potassium salt dihydrate is 2.9%.

3. The method of claim 1 wherein the pH of the solution containing the oxalic acid potassium salt dihydrate is 3.0.

4. A method of desensitizing hypersensitive dentin and cementum comprising applying to the dentin and cementum an effective desensitizing amount of oxalic acid potassium salt, dihydrate in an aqueous solution, the concentration of the oxalic acid potassium salt dihydrate being about 1.5% to about 10% by weight and the solution having a pH in the range of about 2.0 to about 4.0.

5. The method of claim 4 wherein the amount of the oxalic acid potassium salt dihydrate is 2.9%.

6. The method of claim 4 wherein the pH of the oxalic acid potassium salt solution is 4.0.

* * * * *